(12) United States Patent
Chen

(10) Patent No.: US 12,133,662 B2
(45) Date of Patent: Nov. 5, 2024

(54) SKIN GRAFT HARVESTER

(71) Applicant: Timothy Chen, Exton, PA (US)

(72) Inventor: Timothy Chen, Exton, PA (US)

(*) Notice: Subject to any disclaimer, the term of this patent is extended or adjusted under 35 U.S.C. 154(b) by 701 days.

(21) Appl. No.: 17/406,154

(22) Filed: Aug. 19, 2021

(65) Prior Publication Data

US 2022/0054159 A1 Feb. 24, 2022

Related U.S. Application Data

(60) Provisional application No. 63/067,550, filed on Aug. 19, 2020.

(51) Int. Cl.
*A61B 17/322* (2006.01)
*A61B 17/3205* (2006.01)

(52) U.S. Cl.
CPC ...... *A61B 17/322* (2013.01); *A61B 17/32053* (2013.01)

(58) Field of Classification Search
CPC ............ A61B 17/322; A61B 17/32053; A61B 2017/3225
See application file for complete search history.

(56) References Cited

U.S. PATENT DOCUMENTS

| | | | |
|---|---|---|---|
| 3,472,228 A * | 10/1969 | Tanner, Jr. .......... | A61B 17/322 83/346 |
| 3,820,543 A * | 6/1974 | Vanjushin et al. ... | A61B 17/322 606/132 |
| 8,002,779 B2 | 8/2011 | Barker et al. | |
| 8,562,626 B2 | 10/2013 | Sabir et al. | |
| 8,617,181 B2 | 12/2013 | Sabir et al. | |
| 8,926,631 B2 | 1/2015 | Sabir et al. | |
| 8,978,234 B2 | 3/2015 | Sabir et al. | |
| 9,161,776 B2 | 10/2015 | Mahaffey et al. | |
| 9,173,674 B2 | 11/2015 | Sabir et al. | |
| 9,468,459 B2 | 10/2016 | Hall et al. | |
| 9,597,111 B2 | 3/2017 | Sabir et al. | |
| 9,610,093 B2 | 4/2017 | Sabir et al. | |
| 9,848,908 B2 | 12/2017 | Sabir et al. | |
| 10,022,146 B2 | 7/2018 | Esarey et al. | |
| 10,537,355 B2 | 1/2020 | Sabir et al. | |
| 2009/0157095 A1 | 6/2009 | Barker et al. | |
| 2014/0046344 A1 | 2/2014 | Sabir et al. | |
| 2014/0074120 A1 | 3/2014 | Esarey et al. | |
| 2017/0333068 A1* | 11/2017 | Knowlton ......... | A61M 37/0015 |
| 2017/0354434 A1 | 12/2017 | Guiles et al. | |
| 2019/0008542 A1 | 1/2019 | Guiles et al. | |
| 2020/0060715 A1 | 2/2020 | Guiles et al. | |

* cited by examiner

*Primary Examiner* — Anh T Dang
(74) *Attorney, Agent, or Firm* — Joseph E. Maenner; Maenner & Associates, LLC

(57) ABSTRACT

A skin graft tool can cut a skin graft at a desired thickness and width, as desired. A skin punch is provided to cut a perimeter around the area of the skin to be cut for the graft, and a fenestrator tool is provided to fenestrate the cut graft skin material prior to applying to a graft site.

11 Claims, 11 Drawing Sheets

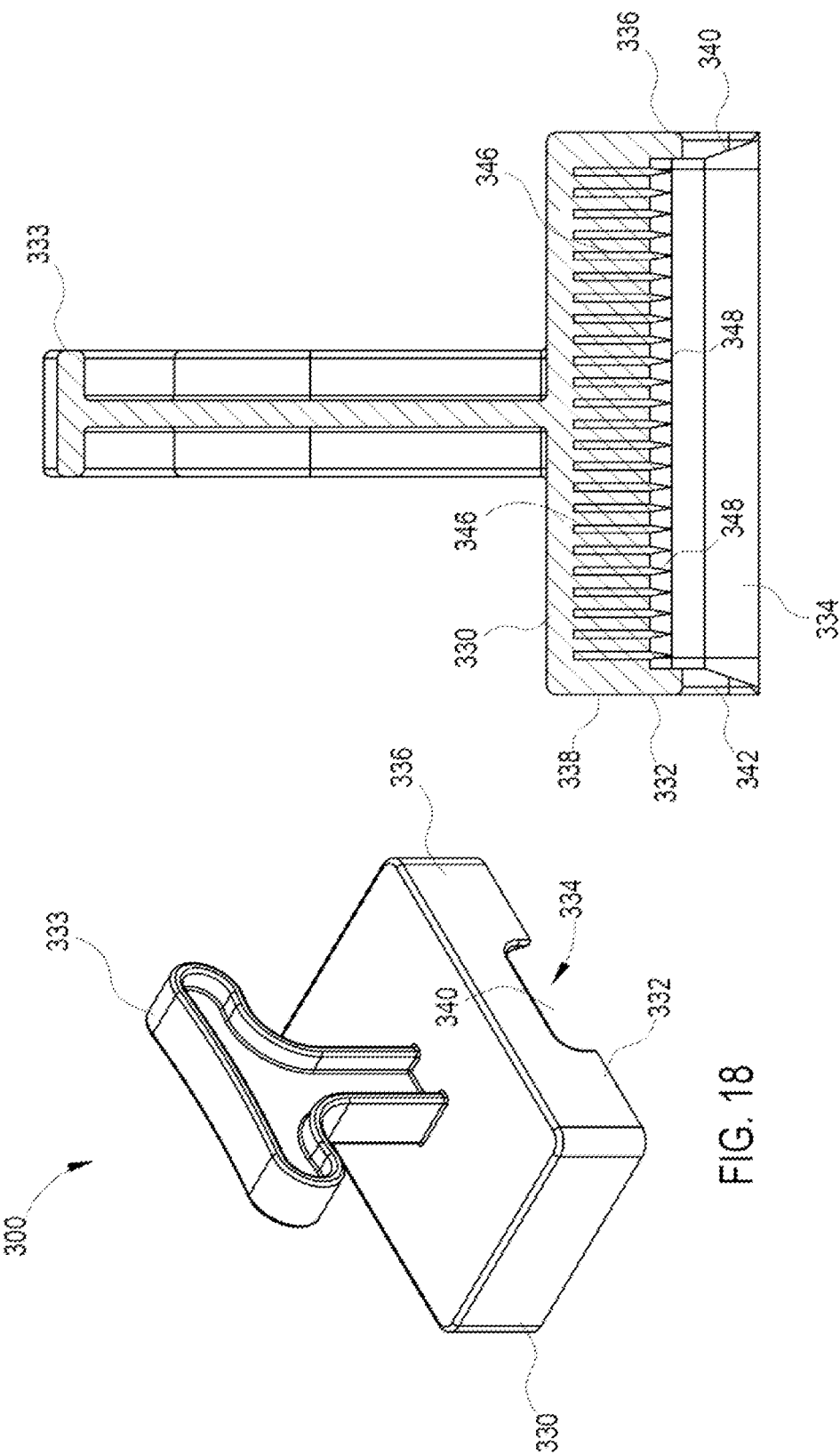

SKIN GRAFT HARVESTER

BACKGROUND OF THE INVENTION

Field of the Invention

The invention relates to a harvesting device for harvesting a skin graft from a patient for subsequent grafting at another location on the patient's body.

Description of the Related Art

When a person experiences a traumatic loss of skin, whether by burns, lacerations, or other types of wounds, it is often beneficial to be able to remove a layer of skin from an unaffected part of the person's body and graft that layer over the affected skin portion. This procedure covers the affected area and also promotes healing. Because it is already part of the person, the grafted skin is accepted by the body, accelerating the healing process. However, different wounds may require different sizes and thicknesses of grafts.

It would be beneficial to provide a skin graft harvesting device that can be adjusted to provide different widths and thicknesses of harvested skin.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a skin graft tool can cut a skin graft at a desired thickness and width, as desired. A skin graft tool comprises a body and a slicing assembly mounted in the body. The slicing assembly comprises a motor having a motor output and an eccentric roller operatively connected to the motor output at a roller input. The eccentric roller has a roller output offset from the roller input. A blade assembly is operatively connected to the roller output such that operation of the motor reciprocates the blade assembly in a side-to-side lateral motion. A blade cover is releasably attached to the body and sized to provide a predetermined width of a cut graft. A thickness guide is releasably attached to the body and sized to provide a predetermined thickness of the cut graft.

In addition, the graft tool can be part of a kit that also includes a skin punch comprising a handle portion and a cutting portion extending downwardly from the handle portion. The cutting portion comprises a cutter body and a cutting blade extending downwardly from the cutter body. The kit further includes a fenestrator comprising a base portion having a top surface sized to allow a harvested graft to be fully placed thereon and a blade portion sized to fit over the base portion. The blade portion has a plurality of blades extending downwardly therefrom such that, when the blade portion is lowered onto the base portion, the plurality of blades penetrate the graft.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 18 is a perspective view of a mesher top portion used with the mesher base of FIG. 17; and FIG. 19 is a side elevational view, in section, of the mesher top portion of FIG. 18.

DETAILED DESCRIPTION

Figure 2:
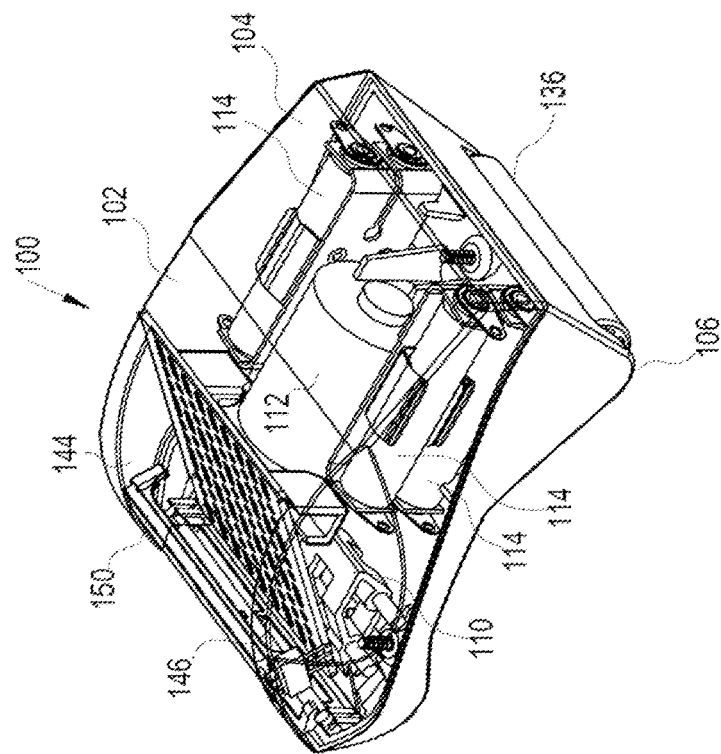
FIG. 2 is a rear perspective view of the tool of FIG. 1, with a top housing portion being see-through to view internal components.
Figure 1:
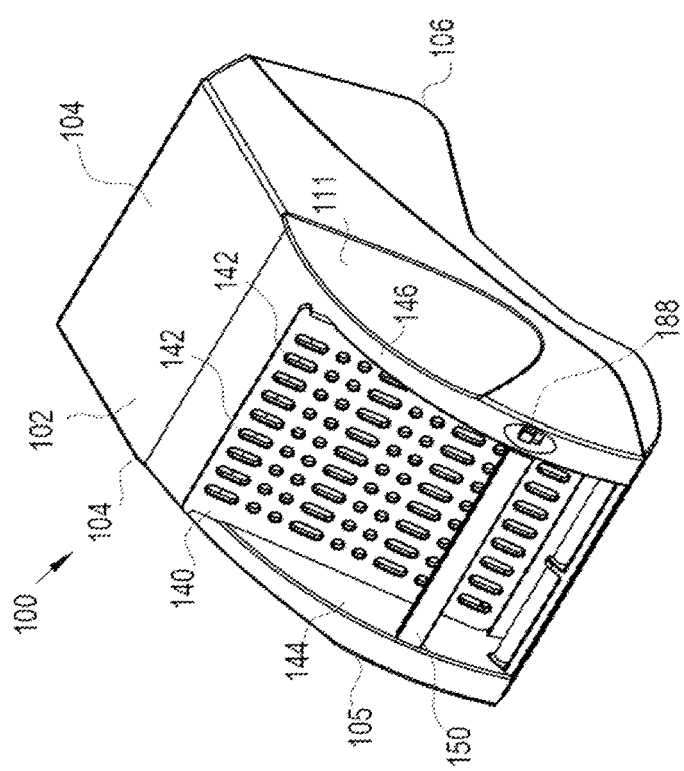
FIG. 1 is a front perspective view of a skin graft tool according to an exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

The present invention provides a skin graft harvester tool for harvesting live skin from a patient for grafting over a location of damaged or removed skin on the same patient. Referring to FIGS. 1-13, a skin graft tool 100 ("tool 100") is a hand-held device that can be grasped and used with a single hand by a user and rolled over a donor skin site to harvest skin graft material for grafting at a different location on the patient. In an exemplary embodiment, tool 100 is about that same size and dimensions as a typical computer mouse.

Referring specifically to FIGS. 1-6, tool 100 includes a housing 102 that supports an oscillating cutting blade assembly 110, a motor 112 to drive blade assembly 110, and batteries 114 to power motor 112. Housing 102 includes a top housing portion 104 and a bottom housing portion 106. Bottom housing portion 106 includes a void 107 (shown in FIG. 4) to raise body 102 upward so the more pressure can be applied toward the front portion 105 of body 102 to aid in cutting the graft.

Blade assembly 110, motor 112 and batteries 114 are mounted on bottom housing portion 106 and covered with top housing portion 104. In an exemplary embodiment, blade assembly 110 cuts the patient's skin at between about a 35-45 degree angle relative to the skin layer. Those skilled in the art will recognize that other angles can be used.

Figure 6:
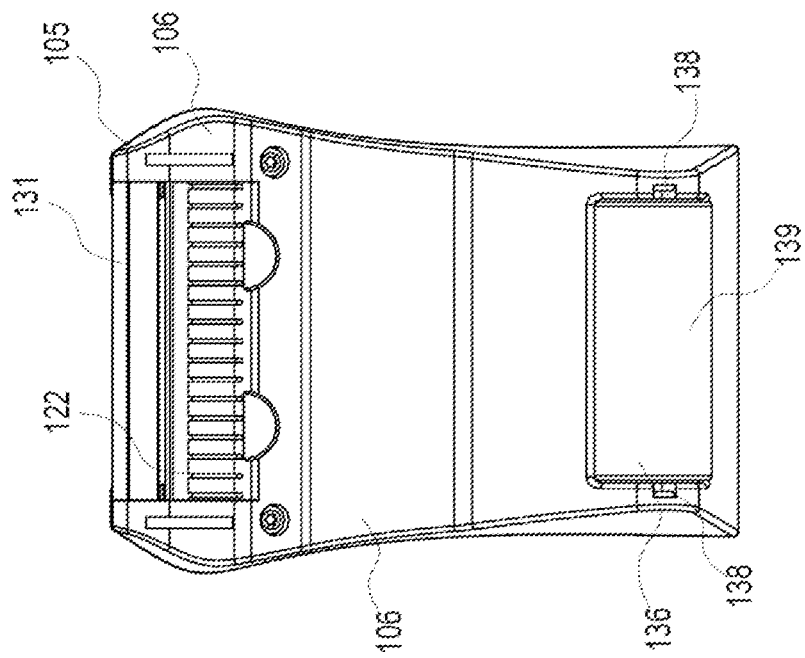
FIG. 6 is a bottom plan view of the tool of FIG. 1 with an exemplary blade cover.
Figure 5:
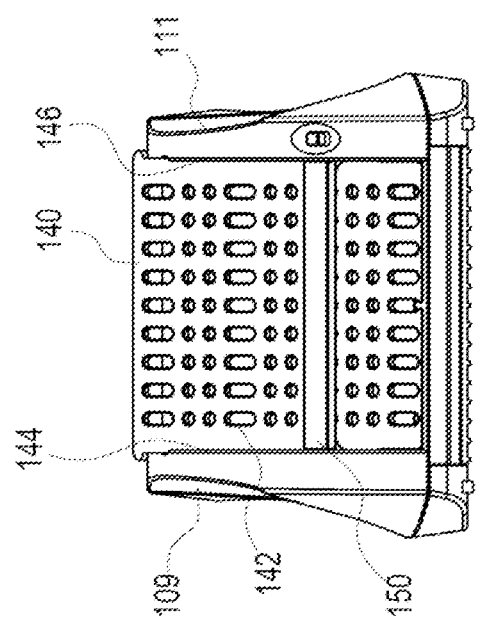
FIG. 5 is a front elevational view of the tool of FIG. 1.
Figure 7:
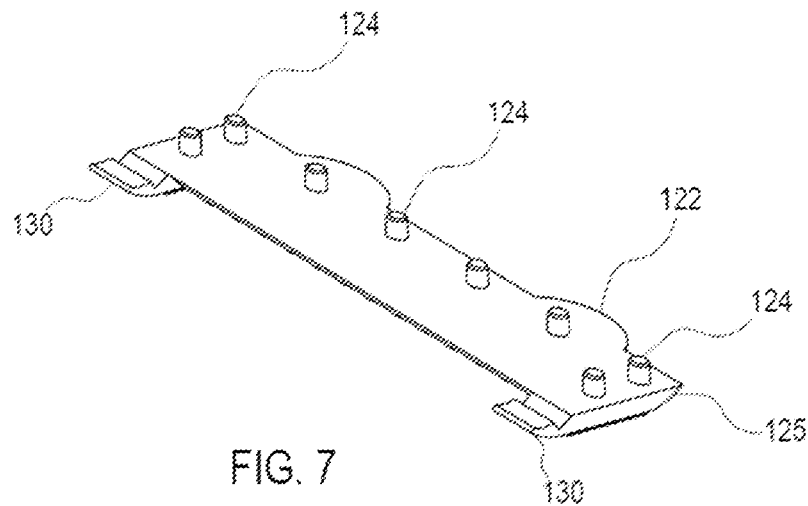
FIG. 7 is a perspective view of the blade cover of FIG. 6.
Figure 7A:
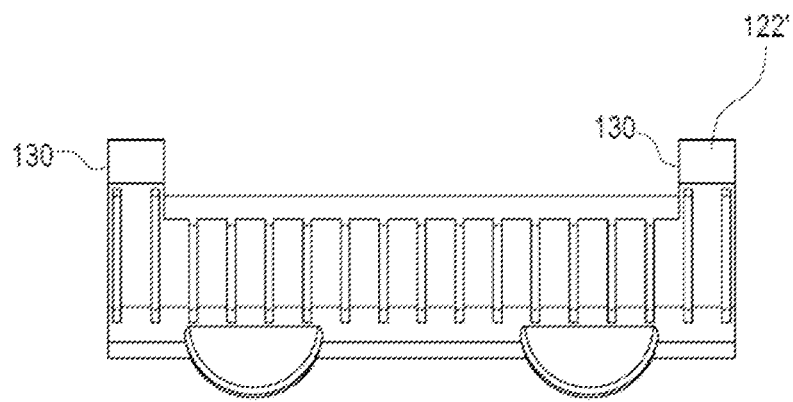
FIG. 7A is a bottom plan view of an alternative embodiment of a blade cover.
Figure 7B:
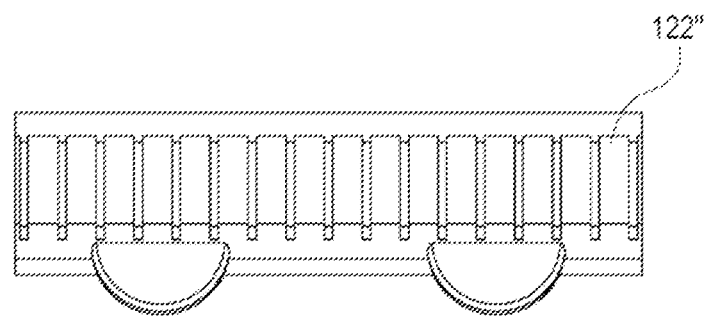
FIG. 7B is a bottom plan view of an alternative embodiment of a blade cover.

Referring to FIG. 6-7B, to adjust the width of the graft, a user can attach one of several blade covers 122, 122', 122" to the underside of bottom housing portion 106. Each blade cover 122, 122', 122" has a predetermined length with a finger 130 extending from each end, perpendicular to the length. Fingers 130 extend parallel to each other and cover a portion of blade assembly 110 such that the covered portion does not cut into the skin as tool 100 is rolled over the skin. Each of blade cover 122, 122' has fingers 130 of differing width so that the distance between fingers 130 determines the width of graft. Blade cover 122" does not include any fingers 130 and provides for the widest graft. To change the width of the graft, a first blade cover 122 can be removed from tool 100 and a second blade cover 122', 122" can be attached to tool 100. In an exemplary embodiment, blade cover 122 yields a graft about 36 mm in width; blade cover 122' yields a graft about 46 mm in width; and blade cover 122" yields a graft about 56 mm in width.

To adjust the width of the graft, blade covers 122 are attached to the underside of bottom housing 104 via pins 124 in the top of each blade cover 122, 122', 122" that slides into corresponding slots in bottom housing portion 106. Pins 124 engage the slots in a slight frictional fit so that pins 124 do not readily slide out of the slots, but blade cover 122 must be pulled from bottom housing portion 106 by the user. A distal end 125 of blade cover 122 has a convex profile, similar to the front of a ski. The convex profile assists in tool 100 gliding over the patient's skin as tool 100 is advanced to cut the graft.

Figure 8:
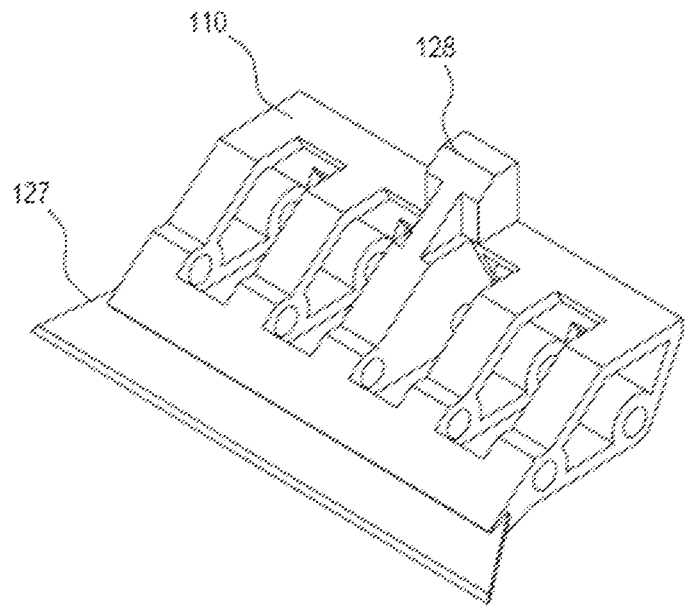
FIG. 8 is a perspective view of a blade assembly used with the tool of FIG. 1.
Figure 9:
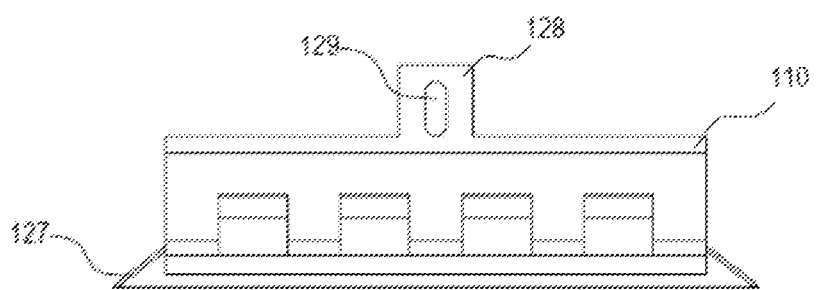
FIG. 9 is a rear elevational view of the blade assembly of FIG. 8.
Figure 10:
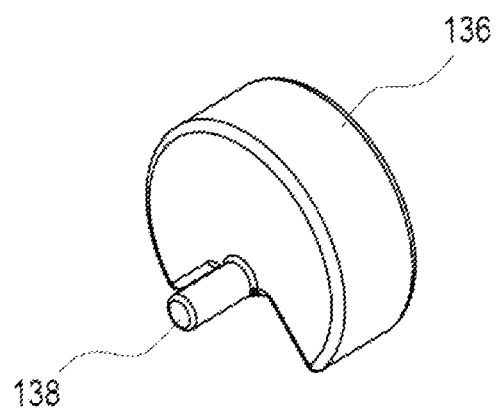
FIG. 10 is a perspective view of an eccentric roller used with the tool of FIG. 1.
Figure 11:
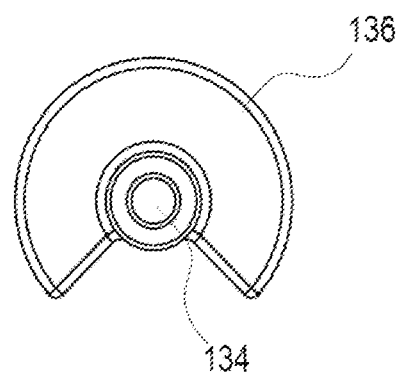
FIG. 11 is a rear elevational view of the eccentric roller of FIG. 11.
Figure 12:
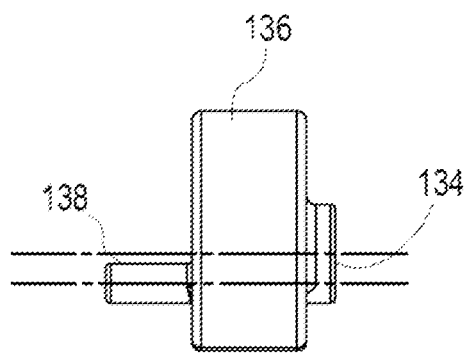
FIG. 12 is a side elevational view of the eccentric roller of FIG. 12.
Figures 13, 13A, 13B:
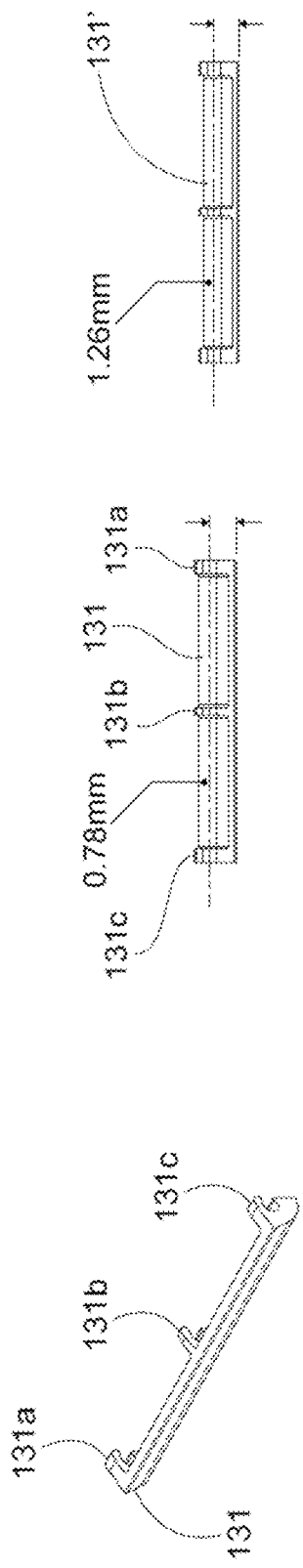
FIG. 13 is a perspective view of a thickness guide used with the tool of FIG. 1.
FIG. 13A is a rear elevational view of the thickness guide of FIG. 13.
FIG. 13B a rear elevational view of an alternative embodiment of the thickness guide of FIG. 13.

Referring back to FIG. 2 and to FIGS. 8 and 9, blade assembly 110 includes a reciprocating blade 127 that slides side-to-side linearly in a lateral direction as motor 112 rotates to cut skin as tool 100 is advanced along donor site. Blade assembly 110 includes a cam riser 128 having an oblong blind opening 129 in the rear thereof (shown in FIG. 9). Blind opening 129 receives an output from motor 130 to reciprocate side-to-side to cut skin when tool 100 is operated.

Referring to FIG. 4 and FIGS. 10-12, motor 112 includes an output shaft 132 that is inserted into an input slot 134 in an eccentric roller 136. Roller 136 has an output shaft 138 that is eccentrically mounted relative to input slot 134 such that, as motor output shaft 132 rotates eccentric roller 136, output shaft 138 describes a circle having a radius equal to the offset of output shaft 138 relative to input slot 134. Output shaft 138 is inserted into blind opening 129 and, as motor shaft 115 rotates, thereby rotating eccentric roller 136, output shaft 138 reciprocates blade 127 side-to-side. The oblong shape of blind opening 129 allows output shaft 138 to describe its circle without blade assembly 110 being lifted up and down.

Referring to FIGS. 4, 6, 13, 14A, 14B, to adjust the thickness of the graft, a thickness guide 131 can be attached to front portion 105 of top housing portion 104 above blade 127. Thickness guide 131 includes mounting stubs 131a, 131b, 131c that allow thickness guide 131 to be releasably mounted onto front portion 105 so that thickness guide 131 can be readily removed. A space 133 is provided between reciprocating blade 127 and the bottom of thickness guide 131, which generates a corresponding thickness in the harvested graft. As shown in FIG. 13A, thickness guide 131 can generate a graft thickness that can be 0.75 mm, while another thickness guide 131', shown in FIG. 13B can generate a graft thickness of 1.25 mm. While two thickness guides 131, 131' are shown, those skilled in the art will recognize that different thickness guides having different thickness ratings can be used.

Referring back to FIG. 2, two batteries 114 are located alone each side of motor 112 and are used to power motor 112. In an exemplary embodiment, batteries 114 can be four 1.5V AAA batteries or equivalent, although those skilled in the art will recognize that other types of batteries can be used.

Figure 4:
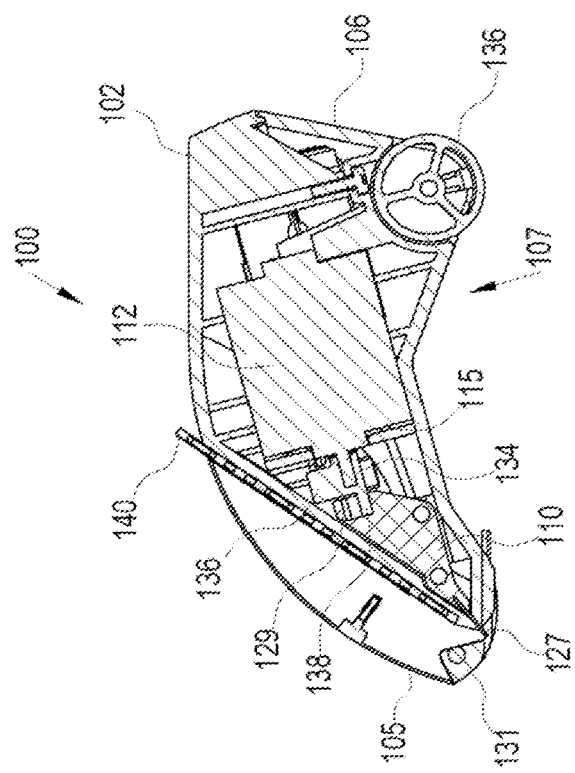
FIG. 4 is a sectional view of the tool of FIG. 3, taken along lines 4-4 of FIG. 3.
Figure 3:
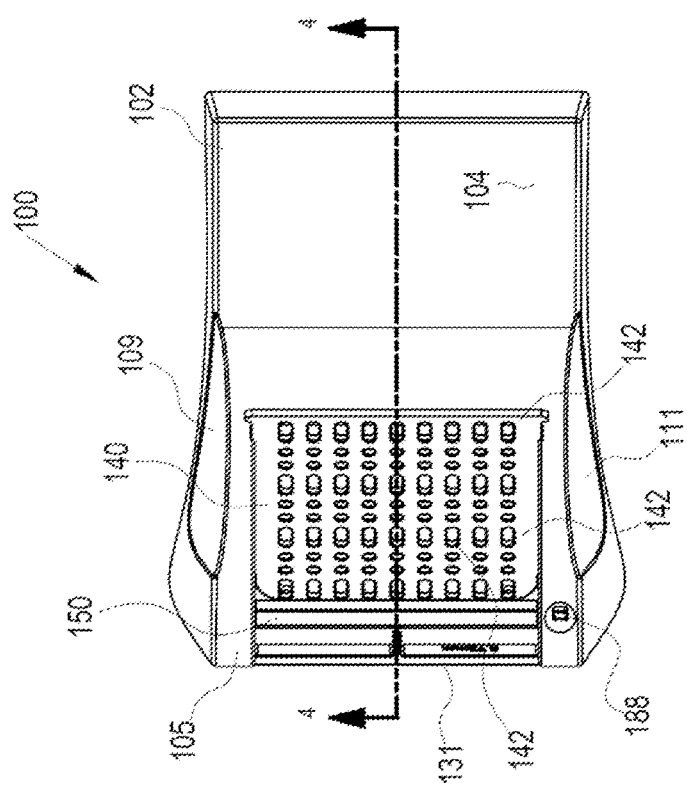
FIG. 3 is a top plan view of the tool of FIG. 1.

Referring to FIGS. 2, 4, 6, a rear roller 136 is rotatingly attached to a rear portion of housing 102 along the bottom of bottom housing portion 106. Rear roller 136 includes an axle shaft 138 extending from either side of a roller body 139 that fits into recesses in lower housing portion 106.

Referring to FIGS. 1 and 3-6, front portion 105 of top housing portion 104 includes a removable graft face 140 that is used to support the graft after the graft has been cut from donor tissue. Graft face 140 extends at an oblique angle from a horizontal plane. Graft face 140 includes a plurality of through-openings 142 that facilitate release of the cut graft from graft face 140.

Interior side walls 144, 146 are provided on either side of graft face 140. Exterior side walls 109, 111 are located outside of interior walls 144, 146, respectively. Exterior side walls 109, 111 are inwardly curved to allow a clinician's thumb and finger to grip tool 100 and advance tool 100 distally across a patient's skin. Additionally, the concavity of the inwardly curved surfaces allows the clinician to apply downward force on tool 100 against the patient's skin.

A bridge 150 extends across and above graft face 140 between side walls 109, 111. Bridge 150 provides support for a clinician's hand on tool 100 as the clinician draws tool 100 across the patient's skin and allows the clinician to apply downward force on tool 100 against the patient's skin.

Referring back to FIGS. 1 and 3, a power switch 188 is used to power motor 112 and cutting blade assembly 110. Switch 188 can be a slide switch, with one position being an "ON" position and an alternate position being an "OFF" position. In an exemplary embodiment, switch 188 can be located on the front portion 105 of housing 102, proximate to bridge 150 to allow a user's right thumb/forefinger easy access to switch 188

Figure 14:
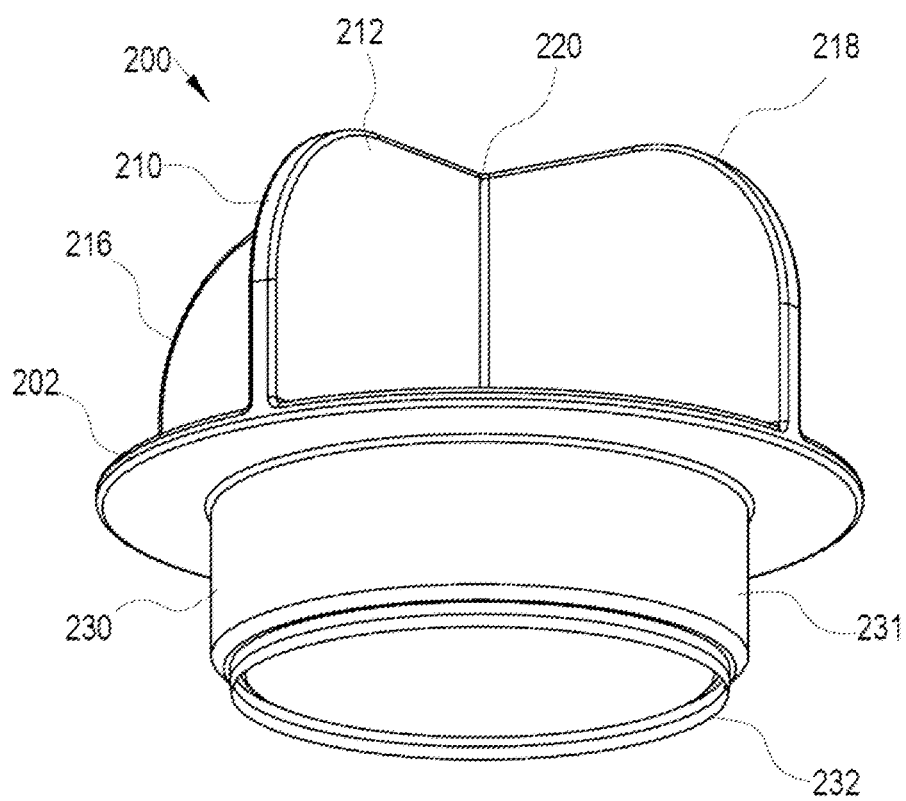
FIG. 14 is a lower perspective view of a skin punch used with the tool of FIGS. 1-13.
Figure 15:
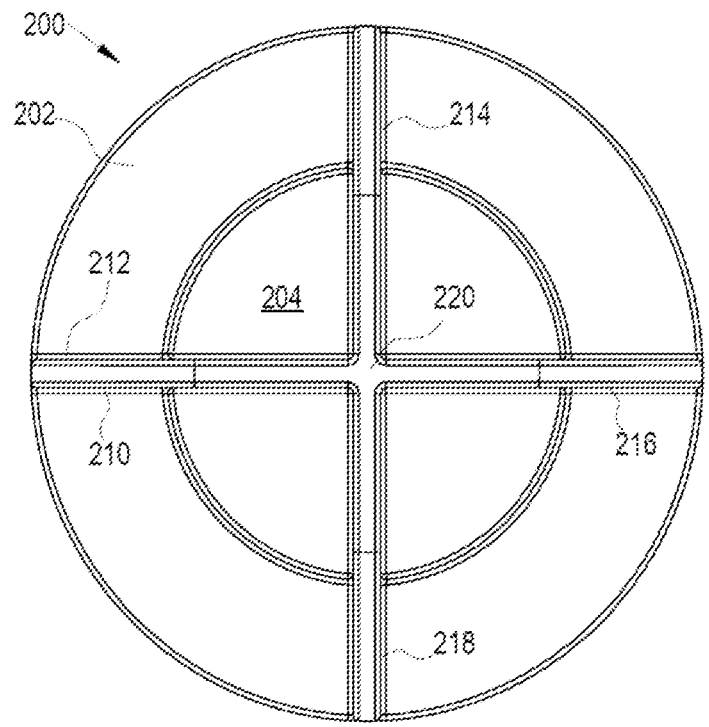
FIG. 15 is a top plan view of the skin punch of FIG. 14.
Figure 16:
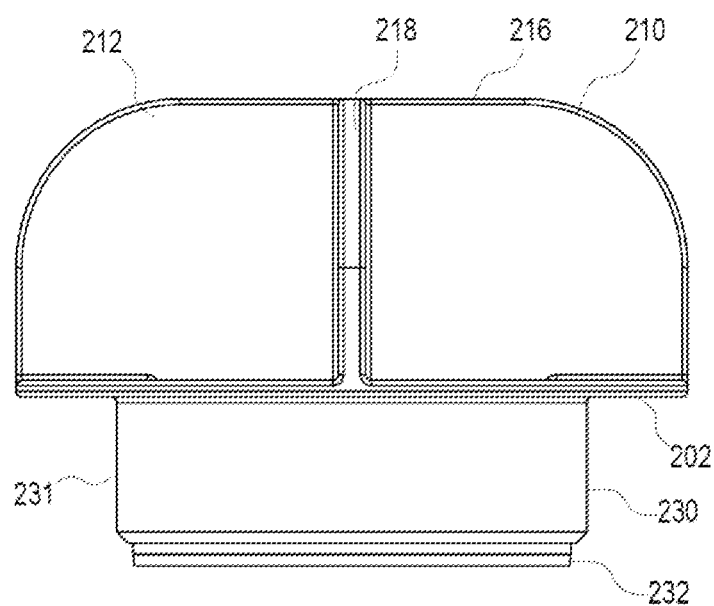
FIG. 16 is a side elevational view of the skin punch of FIG. 14.

Referring now to FIGS. 14-16, a skin punch 200 is shown. Skin punch 200 is used to punch a perimeter of skin that will ultimately be grafted by tool 100. Skin punch 200 is a handheld device that is grasped in one hand and forced down onto the skin of the patient to punch the perimeter.

Skin punch 200 includes a base plate 202. In an exemplary embodiment base plate 202 is generally circular, although those skilled in the art will recognize that base plate 202 can be other shapes as well. An upper, handle portion 210 extends upwardly from base plate 202. Handle portion 210 comprises four orthogonally located walls 212, 214, 216, 218 emanating outwardly from an intersection 220 located at a mid-portion 204 of base 202.

A lower, cutting portion 230 extends downwardly from base plate 202. Cutting portion 230 includes a cutter body 231 having a smaller perimeter than the perimeter of base plate 202.

A cutting blade 232 extends downwardly from cutter body 230. Cutting blade 232 is a continuous blade having a circular perimeter. In an exemplary embodiment, cutting blade 232 can be constructed from stainless steel. In an exemplary embodiment, cutting blade 232 has a diameter of between about 1 cm to about 5 cm, depending on the size of graft desired. Cutting blade 232 extends about 0.030 inches downwardly from cutter body 230.

Figure 17:
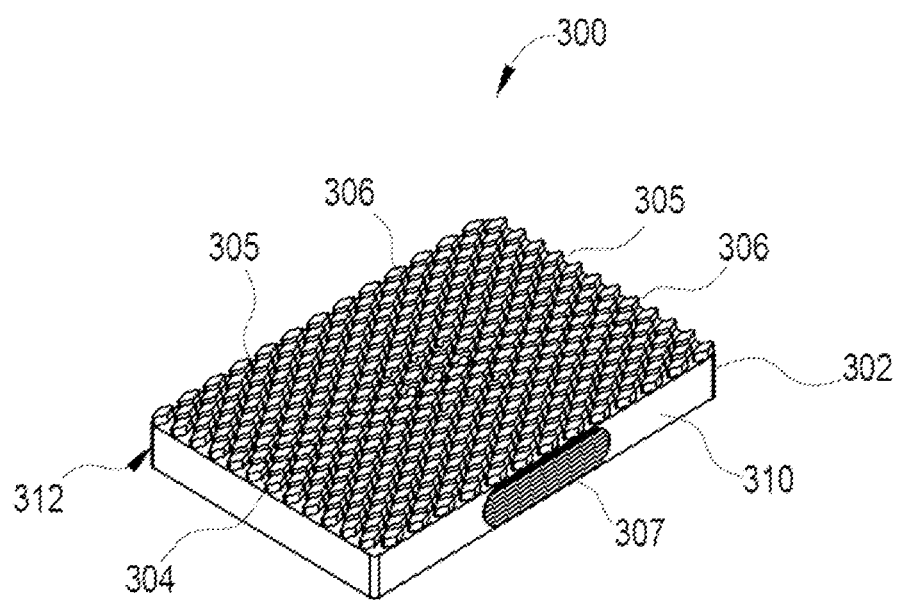
FIG. 17 is a perspective view of a mesher base used with the tool of FIG. 1.

Referring now to FIGS. 17-19, a fenestrator, or mesher, 300 is shown. Mesher 300 is used to fenestrate the graft that has been harvested from the patient prior to grafting the harvested skin onto the damaged skin portion. Fenestrations in the graft allow the graft to expand and to allow blood or other fluid to flow through the graft after the graft is applied to the damaged skin portion of the patient.

Mesher 300 includes a generally rectangular base portion 302 and a blade portion 330. Base portion 302 includes a generally planar top face 304 with a plurality of criss-crossing valleys 305 forming a lattice work. A plurality of generally flat surfaces 306 are formed between valleys 305. Locating tabs 307 extend outwardly from two opposing sides 310, 312, respectively, of base portion 302.

Blade portion 330 fits over base portion 302. Blade portion 330 includes a generally parallelepiped shaped cover 332 with a handle 333 and an open bottom 334. Sides 336, 338 include cutouts 340, 342, respectively, that accommodate locating tabs 307 when blade portion 330 is placed over base portion 302.

A plurality of blades 346 are mounted inside blade portion 320, with sharp ends 348 facing open bottom 334. Blades 346 are parallel to each other and extend downwardly toward open bottom 334 such that sharp ends 348 engage flat surfaces 306 of base portion 302 when blade portion 330 is pressed down over base portion 302.

While tool 100, skin punch 200, and mesher 300 can be provided separately, those skilled in the art will recognize that tool 100, skin punch 200, and mesher 300 can be provided together as a kit, knowing that all of the components of the kit can be single-use only and can be disposed of together after use.

To use tool 100, skin punch 200, and mesher 300, a clinician determines a location on the patient where the graft will be taken from and applies skin punch 200 to that area so that cutting blade 232 cuts the skin, forming the area of skin that will form the graft.

Tool 100 is now used to cut the graft from the patient. Tool 100 is placed on the skin at the location where cutting blade 232 cut the skin. The clinician slides switch 188 to the "ON" position, energizing motor 112 and starting reciprocation of cutting blade assembly 110. Tool 100 is advanced over the skin so that cutting blade assembly 110 can cut the skin. As the skin is cut, the cut skin rides up graft face 140. After the cut graft is on graft face 140, graft face 140 can be removed from the remainder of tool 100.

When the entire skin graft is cut from the patient, the graft is transferred from graft face 140 onto on base portion 302 of mesher 300 and blade portion 330 of mesher 300 is pressed over base portion 302 such that blades 346 engage the graft at locations where the graft is laying on flat surfaces 306 of base portion 302, cutting the graft and forming fenestrations in the graft. The graft is then applied to the patient in the desired location.

It will be further understood that various changes in the details, materials, and arrangements of the parts which have been described and illustrated in order to explain the nature of this invention may be made by those skilled in the art without departing from the scope of the invention as expressed in the following claims.

I claim:

1. A skin graft tool and kit comprising:
   a skin grafter comprising:
      a body;
      a slicing assembly mounted in the body, the slicing assembly comprising:
         a motor having a motor output;
         an eccentric roller operatively connected to the motor output at a roller input, the eccentric roller having a roller output offset from the roller input; and
         a blade assembly operatively connected to the roller output such that operation of the motor reciprocates the blade assembly in a side-to-side lateral motion;
      a blade cover releasably attached to the body and sized to provide a predetermined width of a cut graft; and
      a thickness guide releasably attached to the body and sized to provide a predetermined thickness of the cut graft;
   a skin punch comprising:
      a handle portion; and
      a cutting portion extending downwardly from the handle portion, the cutting portion comprising:
         a cutter body; and
         a cutting blade extending downwardly from the cutter body;
   and
   a fenestrator comprising:
      a base portion having a top surface sized to allow a harvested graft to be fully placed thereon; and
      a blade portion sized to fit over the base portion, the blade portion having a plurality of blades extending downwardly therefrom such that, when the blade portion is lowered onto the base portion, the plurality of blades penetrate the graft.

2. The skin graft tool and kit according to claim 1, wherein the blade cover comprises a first removable blade cover sized to cut a first graft width and wherein the kit further comprises a second removable blade cover sized to cut a second graft width, different from the first graft width.

3. The skin graft tool and kit according to claim 2, wherein the blade cover is located below the blade.

4. The skin graft tool and kit according to claim 1, wherein the thickness guide comprises a first removable thickness guide sized to cut a first graft thickness and wherein the kit further comprises a second removable thickness guide sized to cut a second graft thickness, different from the first graft thickness.

5. The skin graft tool and kit according to claim 4, wherein the thickness guide is located above the blade.

6. The skin graft tool and kit according to claim 1, wherein the blade assembly comprises an oblong opening and wherein the roller output is inserted into the oblong opening such that eccentric rotation of the roller output reciprocates the blade assembly laterally from side-to-side.

7. A method of harvesting a skin graft comprising the steps of:
   (a) providing the graft tool and kit according to claim 1;
   (b) using the skin punch to cut a perimeter of skin to be harvested from a patient;
   (c) using the skin grafter to harvest the skin to be grafted away from the patient;
   (d) placing the cut skin onto the base portion of the fenestrator; and
   (e) lowering the blade portion onto the base portion.

8. The method according to claim 7, further comprising, after step (a) and before step (b), selecting the blade cover from a plurality of blade covers and attaching the selected blade cover to the body.

9. The method according to claim 7, further comprising, after step (a) and before step (b), selecting the thickness guide from a plurality of thickness guides and attaching the selected thickness guide to the body.

10. The method according to claim 7, wherein step (c) comprises eccentrically rotating the roller output to reciprocate the blade assembly laterally from side-to-side.

11. The method according to claim 7, wherein step (e) comprises fenestrating the harvested skin.

* * * * *